United States Patent [19]

Viner

[11] Patent Number: 5,760,049

[45] Date of Patent: Jun. 2, 1998

[54] METHOD FOR CONTROLLING TOBACCO USE AND ALLEVIATING WITHDRAWAL SYMPTOMS DUE TO CESSATION OF TOBACCO USE

[75] Inventor: Norman Viner, Ottawa, Canada

[73] Assignee: Synapse Pharmaceuticals International, Inc., Ottawa, Canada

[21] Appl. No.: 803,723

[22] Filed: Feb. 21, 1997

[51] Int. Cl.⁶ ............ A01N 43/42; A61K 31/44; A24F 47/00

[52] U.S. Cl. ............ 514/291; 514/304; 514/343; 514/640; 514/813

[58] Field of Search ............ 424/408, 464, 424/484, 492; 514/343, 640, 813, 291, 304; 131/270

[56] References Cited

U.S. PATENT DOCUMENTS

| | | |
|---|---|---|
| 2,816,113 | 12/1957 | Wilson et al. |
| 2,996,510 | 8/1961 | Green. |
| 3,063,901 | 11/1962 | O'Leary et al. |
| 3,077,476 | 2/1963 | Hackley, Jr. et al. |
| 3,852,294 | 12/1974 | Hagedorn. |
| 3,877,468 | 4/1975 | Lichtneckert et al. |
| 3,901,248 | 8/1975 | Lichtneckert et al. |
| 3,928,594 | 12/1975 | Cook. |
| 4,002,760 | 1/1977 | Cook. |
| 4,128,651 | 12/1978 | Hagedorn. |
| 4,255,439 | 3/1981 | Cooper. |
| 4,352,810 | 10/1982 | Benschop et al. |
| 4,555,397 | 11/1985 | Bachynsky. |
| 4,596,706 | 6/1986 | Revici. |
| 4,597,961 | 7/1986 | Etscorn. |
| 4,675,326 | 6/1987 | Amitai et al. |
| 4,713,391 | 12/1987 | Chiang et al. ............ 514/412 |
| 4,800,204 | 1/1989 | Mueller. |
| 4,806,356 | 2/1989 | Shaw. |
| 4,832,994 | 5/1989 | Fey. |
| 4,865,837 | 9/1989 | Harris, III et al. |
| 4,925,856 | 5/1990 | Harris, III et al. |
| 4,988,710 | 1/1991 | Olney. |
| 4,999,382 | 3/1991 | Wurtman et al. |
| 5,021,457 | 6/1991 | Akin et al. |
| 5,051,426 | 9/1991 | Parnell. |
| 5,206,371 | 4/1993 | Powers et al. |
| 5,362,496 | 11/1994 | Baker et al. |
| 5,409,946 | 4/1995 | Garvey et al. |
| 5,480,651 | 1/1996 | Callaway. |
| 5,549,906 | 8/1996 | Santus. |
| 5,574,052 | 11/1996 | Rose et al. |
| 5,592,956 | 1/1997 | Ju et al. |
| 5,593,684 | 1/1997 | Baker et al. |
| 5,599,554 | 2/1997 | Majeti. |
| 5,643,391 | 7/1997 | Moormann ............ 514/215 |

FOREIGN PATENT DOCUMENTS

| | | |
|---|---|---|
| 2016920 | 10/1979 | United Kingdom. |
| WO 91/09599 | 7/1991 | WIPO. |

*Primary Examiner*—Ponnathapura Achutamurthy
*Attorney, Agent, or Firm*—James W. Hellwege

[57] ABSTRACT

A method for controlling tobacco use and alleviating withdrawal symptoms due to the cessation of tobacco use comprising administering to a human desiring to control tobacco use and/or suffering from withdrawal due to tobacco use cessation an acetylcholine receptor antagonist and an acetylcholine esterase reactivator as active ingredients in a pharmaceutically acceptable solid matrix material capable of dissolution and/or disentegration in the mouth or the gastrointestinal tract.

26 Claims, No Drawings

METHOD FOR CONTROLLING TOBACCO USE AND ALLEVIATING WITHDRAWAL SYMPTOMS DUE TO CESSATION OF TOBACCO USE

BACKGROUND OF THE PRESENT INVENTION

The present invention is directed to a novel oral drug composition having particular utility in alleviating the symptoms of cessation of tobacco use.

Tobacco use is recognized as constituting a significant health hazard. The particular health hazard may vary depending upon whether the tobacco use results from smoking (i.e., cigarette, cigar and pipe smoking),or from a non-smoking activity (i.e., use of smokeless or chewing tobacco). Many of the health hazards associated with the use of tobacco may be alleviated upon cessation of tobacco use. Even if not totally alleviated, many health risks associated with such use may still be reduced.

Many methods have been proposed and/or attempted to assist persons to reduce or cease tobacco use. See, for example. U.S. Pat. Nos. 3,877,468 (chewable tobacco substitute containing tobacco alkaloid); 3,901,248 (chewable tobacco substitute containing nicotine); 4,255,439 (administration of 2-imidazoline derivative in combination with an anorectic); 4,555,397 (administration of atropine and scopolamine potentiated with chlorpromazine); 4,596,706 (administration of ethylene trithiocarbonate or colloidal sulfur); 4,800,204 (administration of dopamine receptor agonist); 4,806,356 (nicotine lozenge); 4,832,994 (administration of silver acetate); 4,597,961 (transdermal administration of nicotine); 4,999,382 (administration of serotoninergic drugs); 5,021,457 (administration of phenylpropanolamine); 5,051,426 (administration of serotonin antagonist and CNS stimulant); 5,362,496 (sequential transdermal and transmucosal administration of nicotine); 5,409,946 (administration of isoxazole, isothiazole and pyrazole compounds); 5,480,651 (administration of non-specific acetylcholine agonist and a muscarinic agonist); 5,549,906 (lozenge of nicotine, nonnutritive sweetener and an absorbent excipient); 5,574,052 (administration of nicotine receptor activating drug together with antagonist to the nicotine receptor activating drug); 5,592,956 (herbs applied to acupuncture points of body); 5,593,684 (concurrent transdermal and transmucosal administration of nicotine); 5,599,554 (administration of nicotine and caffeine) and WO 91/09599 (administration of inclusion complex of nicotine and cyclodextrin). Psychiatric counseling has also been employed in an attempt to bolster the person's ability to cease or control tobacco use.

Unfortunately, none of the above methods of treatment have been very successful. While such treatments may bring short-term relief to the person, long-term success has not been easily achieved. The degree of success of such methods is generally not predictable due to the fact that the degree of success achieved is dependent upon the susceptibility of the person to the particular treatment employed. In fact, it is believed that some persons are more susceptible to the effects of tobacco use than others with the result that such persons are not easily or readily able to cease such use by means of conventional treatment methods. This is particularly believed to be the case when tobacco use begins during the teenage years and continues into adulthood. Factors such as extent of tobacco use (frequency) and type of tobacco use (smoking vs. non-smoking tobacco use) play a role in the difficulty encountered by a person upon attempting to cease or reduce the extent of tobacco use. Also, comorbid addictions, stress, psychiatric disorders and environmental factors may exacerbate the difficulty encountered by a particular person in ceasing tobacco use. It is believed, for example, that xenobiotic toxic agents such as pesticides, insecticides, fungicides, oxidants, solvents, heavy metals and other environmental toxins encountered by the person by various means (e.g., via drinking water and/or food impurities, etc.) may contribute to the inability of the person to cease or control tobacco use.

OBJECTS AND SUMMARY OF THE PRESENT INVENTION

It is accordingly an object of the present invention to provide an oral drug delivery system which may be used to effectively administer active ingredients to a person.

It is further an object of the present invention to provide a method for the effective administration of an acetylcholine receptor antagonist and an acetylcholine esterase reactivator. It is still further an object of the present invention to provide a method for assisting in the cessation or control of tobacco use as well as alleviating symptoms associated with reduced tobacco use.

In accordance with the present invention, there is thus provided a drug composition for alleviating the symptoms of tobacco use cessation comprising an effective amount of (1) an acetylcholine receptor antagonist and (2) an acetylcholine esterase reactivator. In accordance with the present invention, there is also provided a method for controlling tobacco use and alleviating withdrawal symptoms due to the cessation of tobacco use comprising administering to a human desiring to control tobacco use and/or suffering from withdrawal due to tobacco use cessation an acetylcholine receptor antagonist and an acetylcholine esterase reactivator as active ingredients in a pharmaceutically acceptable solid matrix material capable of dissolution and/or disentegration in the mouth or the gastrointestinal tract.

DETAILED DESCRIPTION OF THE PRESENT INVENTION

The present invention is directed to a drug composition suitable for oral administration comprising an effective amount of (1) an acetylcholine receptor antagonist and (2) an acetylcholine esterase reactivator as well as a method for controlling tobacco use and alleviating withdrawal symptoms due to the cessation of tobacco use comprising administering such a composition to a human desiring to control tobacco use and/or suffering from withdrawal due to tobacco use cessation.

The present invention may be used to control and/or reduce tobacco use of any type. Such tobacco use may result from smoking (i.e., by cigarettes, cigars or pipes) or by use of smokeless or chewing tobacco. It has been found that of the various methods of tobacco use, chronic cigarette and smokeless or chewing tobacco use have been the most difficult to control or cease. Indeed, if begun during the teenage years, such use has been found in the past to be particularly difficult to control or cease. However, by practice of the present invention it is possible for a person who desires to control or cease such use to achieve this goal with a high likelihood of success.

The acetylcholine esterase reactivators which may be employed in the present invention are well known to those skilled in the art and well-described in the literature. Such reactivators found early use as nerve gas and toxic pesticide poisoning antidotes. Exemplary acetylcholine esterase reactivators include but are not limited to those compounds disclosed in U.S. Pat. Nos. 2,816,113; 2,996,510; 3,063,901; 3,077,476; 3,852,294; 3,928,594; 4,002,760; 4,128,651; 4,352,810; 4,675,326; 4,865,837; 4,925,856; 4,988,710; and 5,206,371 each herein incorporated by reference in their entirety.

A preferred class of compounds which may be used as acetylcholine esterase reactivators are oximes, generally defined by the formula $(R^1-CR=NOH)^+X^-$ where R is hydrogen, $C_{1-5}$ alkyl or $NH_2$ and $X^-$ is a pharmaceutically acceptable anion derived from a salt of an inorganic or organic acid. $R^1$ may take many forms. For example $R^1$ may be $C_{1-5}$ alkyl, aryl (e.g., phenyl), or a 5 or 6-membered heterocyclic moiety having from 1 to 3 nitrogen atoms in the heterocyclic ring.

The oxime may also be bicyclic in nature, as defined by the formula $(R^1-CR=NOH)^+X^-$ where R is hydrogen, $C_{1-5}$ alkyl or $NH_2$ and $R^1$ is

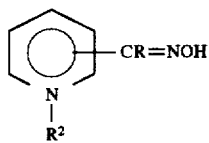

wherein $R^2$ is selected from the group consisting of:

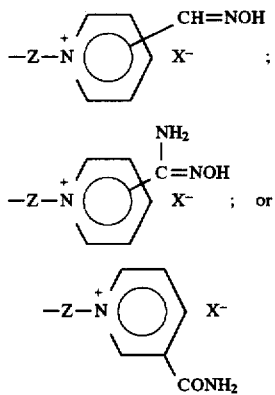

where Z is, for example, a polyalkylene group having from 1 to 6 carbon atoms, optionally including at least one ether linkage, such as —$CH_2CH_2$—, —$CH_2OCH_2$—, —$CH_2CH_2OCH_2CH_2$—, —$CH_2OCH_2CH_2OCH_2$—; or —$(CH_2)n$-phenyl-$(CH_2)n$— where n ranges from 1 to 6 and the phenyl moiety may be substituted by $C_{1-5}$ alkyl, and wherein $X^-$ is a pharmaceutically acceptable anion derived from a salt of an inorganic or organic acid. The above formulae are intended to be merely illustrative and not limiting of the identity of the various types of oximes that may be employed in the present invention. Additional oximes not illustrated above exist which possess the ability to reactivate acetylcholine esterase and which may be employed with advantage in the present invention.

Exemplary acetylcholine esterase reactivators include the following oximes: 2-pyridine aldoxime methiodide, 4-pyridine aldoxime methiodide, methyl-2-pyridyl ketoxime methiodide, 1-methyl-pyridinium-2-aldoxime (2-PAM); 2,3-butanedione-2-oxime (DAM), pyruvaldehyde aldoxime (MINA), 2-pyridine aldoxime methochloride (2-PAM-Cl) (marketed as Protopam chloride), pralidoxime methylsulphate (marketed as Contrathion), obidoxime chloride (marketed as Toxogonin), 1,1'-polymethylene bis (4-formylpyridinium) halide oximes; 1,1'-(2,5-dimethyl-p-phenylenedimethylene) bis (4-formylpyridinium) halide dioximes; 1,1'-polymethylene bis (3-formylpyridinium) halide dioximes; 1,1'-(p-phenylenedimethylene) bis (3-formylpyridinium) halide dioximes; bis quaternary 4-formylpyriinium halide monooximes; 1,1'trimethylene bis (3-amidooximopyridinium) halides, quaternary pyridine aldoxime (TMB-4); HI-6; diacetyl monoxime; aldoxime-substituted triazolium compounds including 1,4-dimethyl-3-(hydroxyimino)methyl-1,2,4-triazolium chloride, 1-benzyl-3-(hydroxyimino)methyl-4-methyl-1,2,4-triazolium chloride, and 3-(hydroxyimino)methyl-1-methyl-4-(2'-methylsulfonyl-1'-ethyl)-1,2,4-triazolium chloride; and aldoxime-substituted imidazolium derivatives such as 1-([1'-(2'-butynyloxy)methyl]-2-(hydroxyimino)methyl-3-methylimidazolium chloride, 2-(hydroxyimino)methyl-3-methyl-1-[1'-2'-(methylsulfonyl) ethyloxy)methyl)-imidazolium chloride, 2-(hydroxyimino)methyl-3-methyl-1-[(2'-methyl-2'-nitropropyloxy)methyl]-imidazolium chloride, 1-[(2'-N,N-dimethylaminium) -1'-ethyl]2-(hydroxyimino) methyl-3-methylimidazolium chloride, 1-[2'-(hydroxyimino) methyl-3'-methyl-1'-imidazolo]-3-(4"-carbamoyl-1"-pyridino) propane dichloride, 1-(3'-bromopropyl-1'-oxy) methyl-2- (hydroxyimino) methyl-3-methylimidazolium chloride, 2-(hydroxyimino)methyl-3-methyl-1- (2'-pyrrdidinium-1'-)ethylimidazolium chloride hydrochloride, 1-(3'-butynyl-1'-thio)methyl-2-(hydroxyimino) methyl-3-methylimidazolium chloride, and 1-[(2'-N-ethyl-N-trifluoromethane sulfonyl) amino-1'-]ethyl-2-hydroxyimino)methyl-3-methylimidazolium chloride.

A preferred class of oximes suitable for use in the present invention may be depicted by the formula:

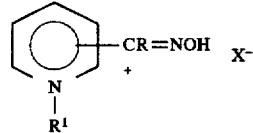

wherein R is hydrogen, $C_{1-5}$ alkyl,or $NH_2$; $R^1$ is $C_{1-5}$ alkyl (particularly methyl or ethyl), and X is an anion portion of the salt $R^1X$. Suitable acid addition salts include the chloride salt, the iodide salt and the methanesulfonate salt.

A specific oxime which is preferred for use in the present invention is 2-PAM chloride which is depicted by the following formula:

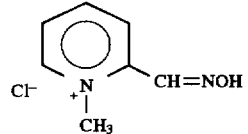

It is also advantageous to administer prodrug derivatives of oximes as disclosed in U.S. Pat. Nos. 3,929,813 and 3,962,447. Such prodrug derivatives exhibit an enhanced ability to pass the blood/brain barrier.

It is believed that oxime-carbamate and oxime carbonate derivatives of oximes as well as hydrazone, semicarbazone and acyl hydrazone derivatives of 2-formyl-1-substituted pyridinium compounds may be usefully employed as acetylcholine esterase reactivators as described in U.S. Pat. Nos. 5,124,455 and 5,206,371, herein incorporated by reference.

The acetylcholine receptor antagonists which are employed in the present invention are well known to those skilled in the art and well-described in the literature. Exemplary antagonists include but are not limited to (singly or in combination) scopolamine, homatropine, atropine, methscopolamine, methylatropine, ipratropium, methylecgonidine (MEG), mecamylamine, benactyzine, benztropine, trihexyphenidyl, biperiden, procyclidine, benzetimide, dexetimide, iaprophen and pharmaceutically acceptable derivatives thereof. See, for example, U.S. Pat. Nos. 5,011,853 and 5,552,407, herein incorporated by reference in their entirety, which disclose exemplary acetylcholine receptor antagonists. Preferred antagonists are scopolamine and ipratropium.

Acetylcholine esterase reactivators (such as 2-PAM and HI-6) have been used in conjunction with acetylcholine receptor antagonists (such as atropine) to provide in vivo protection against nerve gas agents and other organophosphate poisons. See, for example, U.S. Pat. Nos. 3,063,901; 4,713,391; 4,865,837; and 4,925,856. However, an acetylcholine esterase reactivator together with an acetylcholine receptor antagonist have not previously been employed to alleviate the symptoms of withdrawal associated with tobacco use cessation. The amounts of the respective components required to provide the benefits of the present invention are orders of magnitude less than the amounts normally administered to provide protection against nerve gas agents or toxic organophosphate poisoning.

In addition to the acetylcholine esterase reactivator and the acetylcholine receptor antagonist, it is within the scope of the present invention to co-administer additional compounds to assist in achieving the desired result or to provide additional cooperative treatment.

For example, it may be advantageous to administer a stimulant in association with the cholinesterase reactivator and acetylcholine receptor antagonist. A preferred stimulant is nicotine. It has been found that the amount of nicotine administered is less than the amount found in a patch or a stick of nicotine gum (e.g., one milligram or so, the amount not being particularly critical).

Other conventional stimulants (such as dopaminergic stimulants) may be administered in lieu of or in addition to nicotine in the oral composition. Such alternative stimulants include but are not limited to mineptine, Amphetimine, Amphetaminil, Bemegride, Benzphetamine, Brucine, Chorphentermine, Clofenciclan, Clortermine, Cocoa, Demanyl Phosphate, Dexoxadrol, Dextroamphetamine Sulfate (Dexedrine), Diethpropion, N-Ethylamphetamine, Ethamivan, Etifelmin, Etryptamine, Fencamfamine, Fenethylline, Fenosolone, Fenfluramine, Flurothyl, Hexacyclonate Sodium, Homocamfin, Mazindol, Megexamide, Methamphetamine, Methylphenidate, Nicotinic agonists, Nikethamide, Pemoline, Pentylenetetrazole, Phenidimetrazine, Phenmetrazine, Phentermine, Picrotoxin, Pipradrol, Prolintane, Pyrovalerone, and Tetrahydrobenzothienopyridines and mixtures thereof.

Xanthines are an additional class of compounds that may be administered in conjunction with the acetylcholine esterase reactivator and one or more of the other optional active ingredients to assist in signal modulation along the dendrite. U.S. Pat. Nos. 4,364,922; 4,980,379; 5,288,721; 5,340,813; 5,354,756; 5,440,041; 5,473,070; 5,567,704; 5,580,873; and 5,580,874 disclose exemplary xanthines which may be used in the present invention, each herein incorporated by reference. Exemplary xanthines include but are not limited to alkylxanthines such as propylxanthine and methylxanthine. Methylxanthines include 1,3,7-trimethylxanthine (caffeine), 3,7-dimethylxanthine (theobromine), 1,3-dimethylxanthine (theophylline), aminophylline, 1,8-dimethyl-3-(2-methyl-1-butyl)xanthine, 1,3-dimethyl-8-(n-propyl) xanthine, 1,4- (4-hydroxypentyl)-3,7-dimethylxanthine, and 7- (3-phenylpropenyl) theophylline. Exemplary propylxanthines include (E)-4-(1,2,3,6-tetrahydro-1,3-dimethyl-2,6-dioxo-9H-purin-8-yl) cinnamic acid and (E)-4-(1,2,3,6-tetrahydro-2,6-dioxo-1,3-dipropyl-9H-purin-8-yl)cinnamic acid. Prodrug forms of xanthines may also be employed as disclosed in U.S. Pat. Nos. 3,935,196 and 4,061,753, herein incorporated by reference. Such forms exhibit enhanced lipid solubility of the compound.

Adenosine antagonists may also be employed in conjunction with one or more of the above. Such compounds reduce the interstitial concentration of adenosine in myocardial tissue. The compounds may either be a competitive inhibitor or a substance that reduces the concentration of adenosine. A variety of compounds may be used as adenosine antagonists including xanthines (such as those discussed above), imidazopyrimidine, pyraxolopyridine, etazolate, pyrazoloquinoline and triazoloquinazoline. Exemplary adenosine antagonists are described in U.S. Pat. Nos. 4,364,922; 4,980,379; and 5,364,922, each herein incorporated by reference.

As still yet another compound which may be administered in conjunction with one or more of the above is the inhibiting neurotransmitter gamma-aminobutyric acid (GABA) or a precursor thereof such as L-glutamic acid. GABA receptor agonists and other antiepileptics may be employed such as Epival, Baclofen, Sabril, barbiturates, Gabapentin, Lamotrizine and Riluzolo.

It may also be useful to additionally administer an acetylcholine esterase inhibitor such as Phytostigmine, Neostigmine, Demecarium, Pyridostigmine, Velnacrine, Huperzine A, Tacrine, Aricept (Donepezil hydrochloride), Memric, Artane (trihexyphenidyl), Cogentin (benzotropine mesylate), Benedryl (diphenhydramine hydrochloride), Donepezil hydrochloride, etc.

It is within the scope of the present invention to employ both pharmaceutically acceptable analogs as well as tautomers, isomers and salts of the above listed compounds. Analogs differ from the above compounds by means of added alkyl or aryl substituents, added or deleted halogen moieties, presence of differing linkages such as ether linkage, saturation or unsaturation. As to possible salts, the present invention includes within its scope salts of alkali metals, alkaline earth metals, as well as acid addition salts of hydrochloric, hydrobromic, sulfuric, sulfamic, phosphoric, acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, etc.

The oral composition of the present invention may be in any suitable form such as tablets, pills, lozenges, etc. Such compositions may contain the active ingredient(s) in admixture with conventional pharmaceutically acceptable excipients (i.e., inert diluents). Such oral forms of administration may be uncoated or coated by conventional techniques to delay disintegration and absorption in the gastrointestinal tract. More specifically, such oral forms may include an enteric coating to ensure disintegration and absorption in the intestine. Such coatings are generally comprised of a cellulose lower fatty acid phthalate such as cellulose acetate phthalate.

In one embodiment, the acetylcholine receptor antagonist is caused to be administered prior to the administration of the acetylcholine esterase reactivator. Such sequential administration is accomplished by use of a lozenge, tablet, pill, etc. or other suitable form of oral administration which contains the two components in separate layers which permit dissolution and/or disentegration of such layers in sequence in the mouth or the gastrointestinal tract whereby the acetylcholine receptor antagonist is caused to be administered prior to the acetylcholine esterase reactivator.

By way of example, a gelatin-based tablet or pill may be formed of two separate layers. The outermost layer contains the acetylcholine receptor antagonist and the innermost layer contains the acetylcholine esterase reactivator. The gelatin-based tablet or pill may be formed by admixing each active ingredient with the gelatin matrix material. The innermost layer comprised of the gelatin matrix material and the acetylcholine esterase reactivator is formed via conventional molding techniques and permitted to solidify. The outermost layer comprised of additional gelatin matrix material and the acetylcholine receptor antagonist is then formed about the previously-formed inner layer and permitted to solidify about the innermost layer.

The acetylcholine esterase reactivator and the acetylcholine receptor antagonist are present in the oral composition in an amount effective to reduce or prevent the physiological and psychological effects of tobacco withdrawl due to diminished or non-use of tobacco. The phrase "reduce or prevent" is intended to refer to any degree of reduction of the symptoms of withdrawal suffered by the person, as well as any degree of prevention of the suffering of such symptoms if administered prior to the onset of such symptoms. That is, the present invention may be used prophylactically as well as to treat presently existing withdrawal symptoms.

With the above in mind, the various compounds of the present invention may be administered within a wide range of dosage levels while still enabling the benefits of the present invention to be achieved. For example, the acetylcholine receptor antagonist is generally administered at a dosage level of from about 0.001 to 10 mg. The acetylcholine esterase reactivator is generally administered at a dosage level of from about 1 mg to 10 mg. Such dosage levels are based on a standard adult body weight of 70 kg. Additional components such as stimulants are generally administered in amounts of from about 0.1 to 10 mg. The xanthine component, if administered, will generally be administered in an amount of from 25 to 300 mg. Other components that may be co-administered may be administered in conventional amounts. Such dosage administrations are repeated as required to provide the desired results, with administrations being repeated every 12 to 36 hours depending upon the extent of withdrawal symptoms observed.

The present invention is illustrated by the following examples which are not intended to be limiting of the scope of the invention but merely illustrative of various preferred and specific embodiments.

EXAMPLE 1

A forty year old male with a twenty five year smoking history of moderate intensity and a desire to cease smoking cigarettes was orally administered an acetylcholine receptor antagonist (scopolamine) followed by oral administration of an acetylcholine esterase reactivator (2-PAM-Cl), each in a pharmaceutically acceptable solution. A nicotine patch was placed on the person's torso immediately prior to the administration of the two compounds. The scopolamine was administered within the dosage range of from 0.001 to 10 mg. and the 2-PAM-Cl was administered within the dosage range of from 2 to 8 mg. The person experienced a relatively immediate lack of desire to use tobacco (in this instance the smoking of cigarettes). The ability to control the desire to smoke a cigarette continued for 8 hours. Similar results were observed upon administration of the two compounds in the form of a tablet in which the two compounds were administered in sequentially dissolved layers, with the scopolamine being the outermost layer.

EXAMPLE 2

A 39 year old male smoker (1–2 packs per day) with a 25–30 pack year smoking history was highly motivated to quit smoking. He was given 5 mgs of protopam on mnultiple occasions following either (1 mg nicotine and 0. 1 mg scopolamine) or (1 mg nicotine and 0. 1mg ipratropium) via the oral mucosa by drops and gum. The individual reported that he remained withdrawal symptom free for periods of time ranging from 6–36 hours. As a followup, he was placed on a lozenge containing an outer shell of 0.1 mg of either ipratropium or scopolamine with an inner shell of protopam 2.5 mg. On a bid dosage of either lozenge combined with a nicotine patch he was able to remain smoke free without any significant withdrawal symptoms or urges to smoke for the ten day trial period.

From the above description, one of ordinary skill in the art can readily ascertain the essential characteristics of the present invention. Without departing from the scope of the invention, various changes and/or modifications can be made which are still within the scope and range of equivalence of the attached claims.

What is claimed is:

1. A method for controlling tobacco use and alleviating withdrawal symptoms due to the cessation of tobacco use comprising orally administering to a human desiring to control tobacco use and/or suffering from withdrawal due to cessation of such use an effective amount of each of (1) an acetylcholine receptor antagonist and (2) an acetylcholine esterase reactivator as active ingredients in a pharmaceutically acceptable solid matrix material capable of-dissolution and/or disentegration in the mouth or the gastrointestinal tract.

2. The method of claim 1 wherein said acetylcholine receptor antagonist is selected from the group consisting of scopolamine, homatropine, atropine, methscopolamine, methylatropine, ipatropium, mecamylamine and mixtures thereof.

3. The method of claim 1 wherein said acetylcholine esterase reactivator is selected from the group consisting of an oximes a pharmaceutically acceptable prodrug derivative thereof and a pharmaceutically acceptable salt thereof.

4. The method of claim 3 wherein said oxime is selected from the group consisting of monoquaternary oximes, bisquaternary oximes, and triquaternary oximes.

5. The method of claim 1 wherein said acetylcholine esterase reactivator is an oxime salt.

6. The method of claim 5 wherein said salt is an acid addition salt selected from the group consisting of a chloride, iodide and methanesulfonate salt.

7. The method of claim 6 wherein said acetylcholine esterase reactivator is a chloride salt of an oxime.

8. The method of claim 7 wherein said acetylcholine esterase reactivator is 2-pyridine aldoxime methochloride (2-PAM Cl).

9. The method of claim 1 wherein said acetylcholine esterase reactivator is s elected from the group consisting of 1-methyl-pyridinium-2-aldoxime (2-PAM), 2,3-butanedione-2-oxime (DAM), pyruvaldehyde aldoxime (MINA), bis quaternary pyridine aldoxime (TMD-4), pharmaceutically acceptable prodrug derivatives thereof and pharmaceutically acceptable salts thereof.

10. The method of claim 1 wherein a stimulant is administered in conjunction with said acetylcholine receptor antagonist and said acetvlcholine esterase reactivator.

11. The method of claim 10 wherein said stimulant is selected from the group consisting of nicotine, muscarine, arecoline, lobeline, cotinine, kat, nikethamide, ethamivan, bethanechol, pilocarpine, and mixtures thereof.

12. The method of claim 10 wherein said stimulant is nicotine.

13. The method of claim 1 wherein said acetylcholine receptor antagonist is selected from the group consisting of scopolamine and ipratropium, and said acetylcholine esterase reactivator is selected from the group consisting of an oxime, a pharmaceutically acceptable prodrug derivative thereof and a pharmaceutically acceptable salt thereof.

14. The method of claim 13 wherein said acetylcholine receptor antagonist is scopolamine and said acetylcholine esterase reactivator is 2-pyridine aldoxime methochloride (2-PAM Cl) or a pharmaceutically acceptable prodrug derivative thereof.

15. The method of claim 14 wherein nicotine is administered in conjunction with said acetylcholine receptor antagonist and said acetylcholine esterase reactivator.

16. The method of claim 13 wherein said acetylcholine receptor antagonist is ipratropium and said acetylcholine esterase reactivator is 2-pyridine aldoxime methochloride (2-PAM Cl) or a pharmaceutically acceptable prodrug derivative thereof.

17. The method of claim 16 wherein nicotine is administered in conjunction with said acetylcholine receptor antagonist and said acetylcholine esterase reactivator.

18. The method of claim 1 wherein said acetylcholine esterase reactivator is defined by the formula $(R^1\text{---}CR=NOH)^+X^-$ where R is hydrogen, $C_{1-5}$ alkyl or $NH_2$, $R^1$ is $C_{1-5}$ alkyl and $X^-$ is a pharmaceutically acceptable anion derived from a salt of an inorganic acid or a salt of an organic acid.

19. The method of claim 1 wherein said acetylcholine esterase reactivator is defined by the formula $(R^1\text{---}CR=NOH)^+X^-$ where R is hydrogen, $C_{1-5}$ alkyl or $NH_2$, $R^1$ is aryl and $X^-$ is a pharmaceutically acceptable anion derived from a salt of an inorganic acid or a salt of an organic acid.

20. The method of claim 1 wherein said acetylcholine esterase reactivator is defined by the formula $(R^1\text{---}CR=NOH)^+ X^-$ where R is hydrogen, $C_{1-5}$ alkyl or $NH_2$ and $R^1$ is a 5 or 6 membered heterocyclic moiety having from 1 to 3 nitrogen atoms in the heterocyclic ring and X is a pharmaceutically acceptable anion derived from a salt of an inorganic acid or a salt of an organic acid.

21. The method of claim 1 wherein said acetylcholine esterase reactivator is defined by the formula $(R^1\text{---}CR=NOH)^+ X^-$ where R is hydrogen, $C_{1-5}$ alkyl or $NH_2$ and $R^1$ is

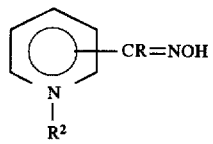

wherein $R^2$ is selected from the group consisting of:

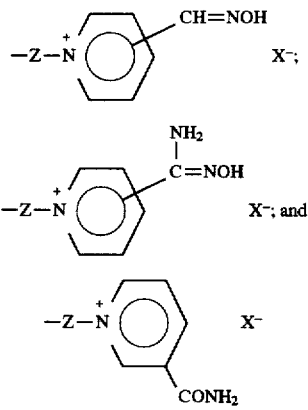

where Z is a polyalkylene group having from 1 to 6 carbon atoms, optionally including at least one ether linkage, or —$(CH_2)$n-phenyl-$(CH_2)$n— where n ranges from 1 to 6 and the phenyl moiety may be optionally substituted by $C_{1-5}$ alkyl, and wherein $X^-$ is a pharmaceutically acceptable anion derived from a salt of an inorganic acid or a salt of an organic acid.

22. The method of claim 1 wherein said acetylcholine esterase reactivator is administered in an amount within the range of from about 1 to 10 mg per 70 kg body weight.

23. The method of claim 1 wherein said acetylcholine receptor antagonist is administered in an amount within the range of from about 0.001 to 10 mg. per 70 kg body weight.

24. The method of claim 1 wherein said matrix material is gelatin.

25. The method of claim 1 wherein said tobacco is in the form of cigarettes.

26. The method of claim 1 wherein said tobacco is in the form of smokeless or chewing tobacco.

* * * * *